(12) United States Patent
Matthys

(10) Patent No.: US 7,713,289 B2
(45) Date of Patent: May 11, 2010

(54) DEVICE FOR FIXING A LONGITUDINAL CARRIER TO A BONE FIXING ELEMENT

(75) Inventor: Romano Matthys, Davos Clavadel (CH)

(73) Assignee: Synthes USA, LLC, West Chester, PA (US)

( * ) Notice: Subject to any disclaimer, the term of this patent is extended or adjusted under 35 U.S.C. 154(b) by 900 days.

(21) Appl. No.: 11/339,810

(22) Filed: Jan. 24, 2006

(65) Prior Publication Data
US 2006/0173455 A1 Aug. 3, 2006

Related U.S. Application Data

(63) Continuation of application No. PCT/CH03/00516, filed on Jul. 29, 2003.

(51) Int. Cl.
*A61B 17/70* (2006.01)
(52) U.S. Cl. .............. 606/264; 606/246; 606/278; 606/279
(58) Field of Classification Search .......... 606/246, 606/264–279; 411/399, 425
See application file for complete search history.

(56) References Cited

U.S. PATENT DOCUMENTS

| | | | |
|---|---|---|---|
| 4,920,959 A | | 5/1990 | Witzel et al. |
| 4,946,458 A | | 8/1990 | Harms et al. |
| 5,290,288 A | | 3/1994 | Vignaud et al. |
| 5,527,314 A | * | 6/1996 | Brumfield et al. ......... 606/278 |
| 5,534,002 A | * | 7/1996 | Brumfield et al. ......... 606/278 |
| 5,662,651 A | * | 9/1997 | Tornier et al. ............. 606/60 |
| 5,676,665 A | | 10/1997 | Bryan |
| 6,206,881 B1 | * | 3/2001 | Frigg et al. ............... 606/291 |
| 6,248,104 B1 | * | 6/2001 | Chopin et al. ............. 606/267 |
| 6,482,207 B1 | * | 11/2002 | Errico ...................... 606/264 |

FOREIGN PATENT DOCUMENTS

| | | |
|---|---|---|
| CH | 632 658 | 10/1982 |
| DE | 195 34 136 A1 | 3/1996 |
| FR | 2 775 587 | 9/1999 |
| JP | 2001299771 | 10/2001 |
| WO | WO 98/43551 | 10/1988 |
| WO | WO 94/01049 | 1/1994 |
| WO | WO 95/13754 | 5/1995 |
| WO | WO 01/19267 | 3/2001 |

OTHER PUBLICATIONS

Australian Patent Office Examiners First Report dated Feb. 8, 2008.
Notice of the Reason for the Preliminary Rejection issued by Japanese Patent Office on Jun. 3, 2009.

* cited by examiner

*Primary Examiner*—Eduardo C Robert
*Assistant Examiner*—Steven J Cotroneo
(74) *Attorney, Agent, or Firm*—Stroock & Stroock & Lavan LLP

(57) ABSTRACT

The device is used for mutually securing or clamping a longitudinal carrier (e.g., a spinal rod) to a bone fixing element (e.g., a pedicle screw). The device includes a body having a channel that is open along its longitudinal axis on one side for receiving the longitudinal carrier. The body has a bore that extends fully through the body and at least partially intersects the channel. The bore is conical in form and has a large opening, a small opening, and an inner thread. The head of the bone fixing element has an outer thread that corresponds to the inner thread. As the fixing element is secured in the bore, it locks the longitudinal carrier to the device.

10 Claims, 2 Drawing Sheets

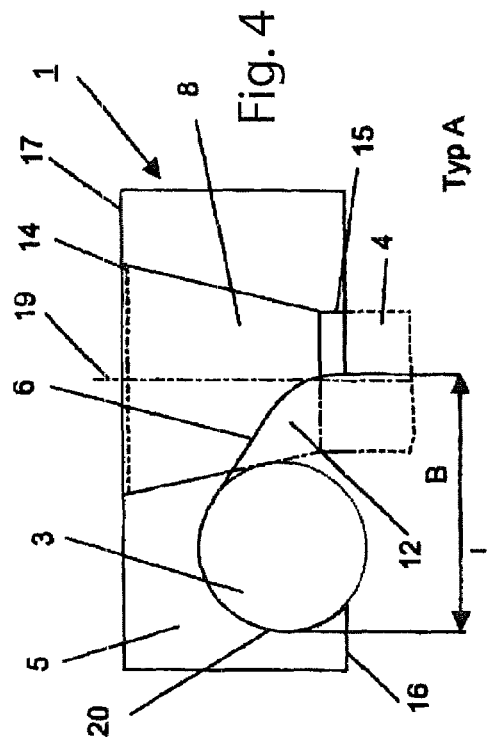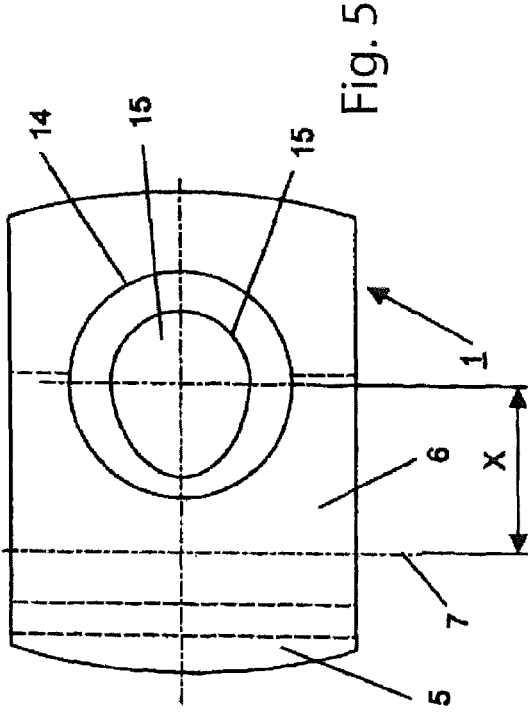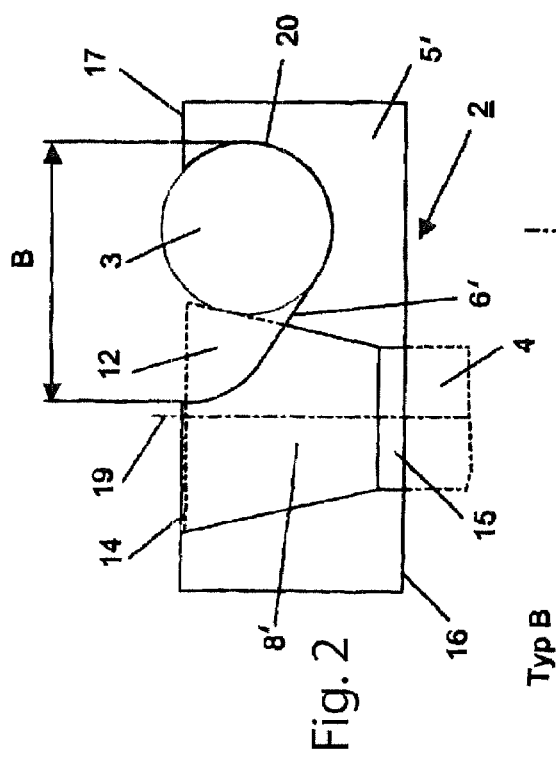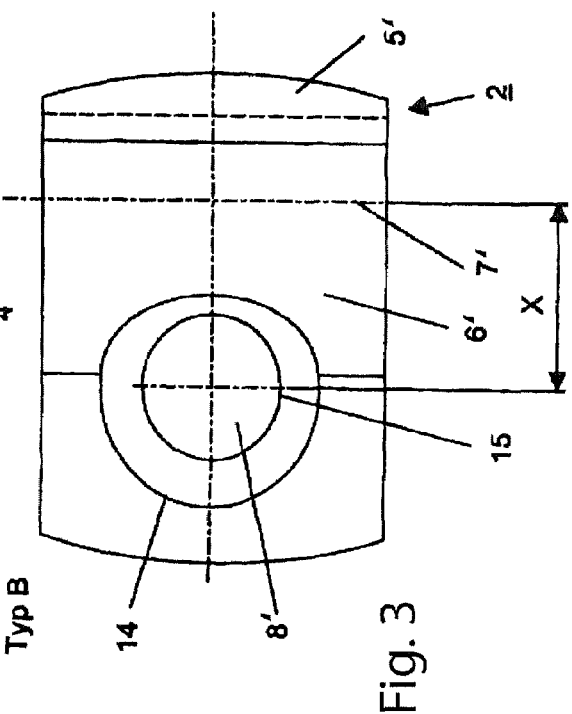

DEVICE FOR FIXING A LONGITUDINAL CARRIER TO A BONE FIXING ELEMENT

CROSS REFERENCE TO RELATED APPLICATION

This is a continuation of International Patent Application No. PCT/CH2003/00516, filed Jul. 29, 2003, the entire contents of which are incorporated herein by reference thereto.

TECHNICAL FIELD OF THE INVENTION

The invention relates to a device for mutually securing a longitudinal carrier and a bone fixing element. With such devices, a spinal or connecting rod (i.e., a longitudinal carrier), such as that used in spinal surgery, can be connected over a bone fixing element (preferably a bone screw) to obtain a rigid construct.

BACKGROUND OF THE INVENTION

Witzel et al. U.S. Pat. No. 4,920,959 discloses an external fixture which is relatively cumbersome. It includes twin-rod holders, a pair of longitudinal fixture frame rods, a bone screw for each rod holder, and operating screws for fixing the bone screws to the rods. A disadvantage of the individual twin-rod holders (i.e., the clamping elements) is that they apparently mount onto the longitudinal rods from only the ends of the rods.

Swiss Patent No. CH 632 658 discloses an implant for fixing bones. The quality of the disclosed locking device depends directly on the pretensioned force, which can be realized between the Briden body and the bone. Here also, if the implant is used as a clamp, the individual clip body (i.e., clamp element) apparently mounts onto two parallel longitudinal rods from only the ends of the rods (lateral mounting is apparently not possible). This mounting may be difficult to realize in the case of a freehand application, particularly a percutaneous and minimally invasive application, and represents a major disadvantage.

On the other hand, Vignaud et al. U.S. Pat. No. 5,290,288, WO 94/01049, and French Patent No. FR 2 775 587 all disclose open clamps in which a longitudinal carrier can be laterally mounted. However, they all have the disadvantage of requiring an additional element (e.g., a nut) for their fixation. Furthermore, the clamp holding device is the bone screw itself, which typically must first be fixed in the bone before the longitudinal carrier can be placed on the bone screw.

Finally, WO 95/13754 discloses a clamp in which a longitudinal rod can be introduced laterally into an open channel of the clamp. The rod can then be secured by means of a set screw, which passes through the clamp. However, the set screw has only this one function and cannot be used, for example, as a bone screw that could fasten the whole construct at the bone. The same is also true for the holding device disclosed in German Patent No. DE 195 34 136.

Accordingly, known devices can be quite complicated having little flexibility with respect to their application.

In view of the foregoing, it is an object of the invention to provide a device that has a very simple structure and that can be used flexibly and in minimally invasive surgical techniques.

SUMMARY OF THE INVENTION

The object of the invention is accomplished with a device having a channel for receiving a longitudinal carrier and a bore partially intersecting the channel. The bore has a conical shape for receiving the head of a fixation element after the body of the fixation element has passed through the bore. As the fixation element is secured in the bore, it locks the longitudinal carrier to the device.

The advantages of the inventive device are many and preferably include the following:

it is only one part;
it can be used in minimally invasive techniques and does not require a large opening;
prestressing between the device and the bone is not necessary to ensure locking;
it can be used as an external fixator as well as for an internal fixator;
the longitudinal carrier can be positioned in the device from the very start and pre-shaped, and the user can then set the bone screw when an appropriate position is determined;
the position of the individual devices can be freely selected by the user;
additional devices, if required, can simply be laterally slipped onto the longitudinal carrier without having to be moved laboriously over the whole length of the longitudinal carrier;
before the inventive devices are set, the longitudinal carrier can be brought in to give the surgeon an opportunity to determine more easily the screw positions;
setting a fracture over a longitudinal carrier is possible;
a user can connect and fix the individual fracture parts by a minimally invasive technique over a construct of a longitudinal carrier and several inventive devices by means of angularly stable head locking screws; and
the inventive device can be used not only in spinal column applications, but also in other osteosynthetic applications.

The inventive device accommodates a longitudinal carrier and a standard head-locking screw corresponding to the device's conically-shaped bore. When the head-locking screw is tightened, it locks the longitudinal carrier in the inventive device.

The bore in the device has a conical angle ranging from 5° to 25° and preferably from 8° to 15°.

The inventive devices, realized in the form of clamps, may be of two different embodiments, type A and type B. They differ in that one can be mounted from above (type A) a longitudinal carrier (e.g., a connecting rod) and the other from below (type B) a longitudinal carrier. The locking principle is the same for both. For type A, the conical bore tapers inward towards the channel and the smaller opening of the bore is on the same side of the body of the device as the channel. The device can be advantageously slipped laterally on top of an already positioned and/or secured longitudinal rod. For type B, the conical bore expands toward the channel and the larger opening of the bore is on the same side of the body as the channel. The longitudinal carrier can be advantageously introduced laterally into a type B device already coupled to a bone fixation element.

In one embodiment, the device additionally includes a bone fixation element, preferably in the form of a bone screw having a tip, a threaded shaft, and a head. The head is suitable for manipulating the screw, and the tip is suitable for insertion into the bone. This permits the setting of bone fragments via the bone screw.

The head of the bone fixation element has an external thread, which corresponds to an internal thread of the bore. This preferably ensures the least possible material abrasion during the fixation. The pitch of the external thread may be 0.1 to 3.0 mm and preferably is 0.25 to 1.50 mm.

The head of the bone fixation element tapers conically towards the tip. The conically tapering head may have a conical angle ranging from 5° to 25° and preferably from 8° to 15°.

In another embodiment, a type A device may be combined with a type B device. Such a combination has the advantage of forming a rigid frame together with the treated bone.

A general method of operation for the inventive device includes the following:

The longitudinal carrier is introduced through a stab incision into the region of the patient that is to be treated. The carrier is then pushed percutaneously into the desired position. The surgeon can now contour the longitudinal carrier appropriately. When the contour of the carrier is satisfactory, the desired number of inventive devices can be introduced percutaneously through corresponding stabbed incisions and mounted laterally directly on the carrier. The angularly stable head-locking screws can now be screwed into the bores of the inventive devices, but not yet tightened. When the setting is satisfactory, the angularly stable head locking screws can then be tightened so that the construct, formed from the longitudinal carrier, the inventive devices, and the bone screws, becomes rigid and the fracture is fixed.

A more particular method of operation for the inventive device includes the following:

A type B inventive device is positioned relative to the affected bone part, and a head-locking screw is screwed through the conical bore of the type B device to a predetermined depth, so that the device is pre-fixed. The longitudinal carrier is then contoured to meet anatomical requirements and inserted in the open channel of the already pre-mounted type B device. The head-locking screw can now be tightened completely in the type B device, so that the longitudinal carrier is fixed at the device. The fracture is set over the longitudinal carrier with a suitable setting instrument, and the set bone fragments are fixed by means of type A or type B devices. The bone fixation construct optionally is supplemented with additional type A or type B devices.

BRIEF DESCRIPTION OF THE DRAWINGS

The detailed description will be better understood in conjunction with the accompanying drawings, in which like reference characters represent like elements, as follows:

FIG. 2 is an elevational view of an inventive device of type B;

FIG. 3 is a plan view of the device of FIG. 2;

FIG. 4 is an elevational view of an inventive device of type A; and

FIG. 5 is a plan view of the device of FIG. 4.

DETAILED DESCRIPTION OF THE INVENTION

Figure 1:
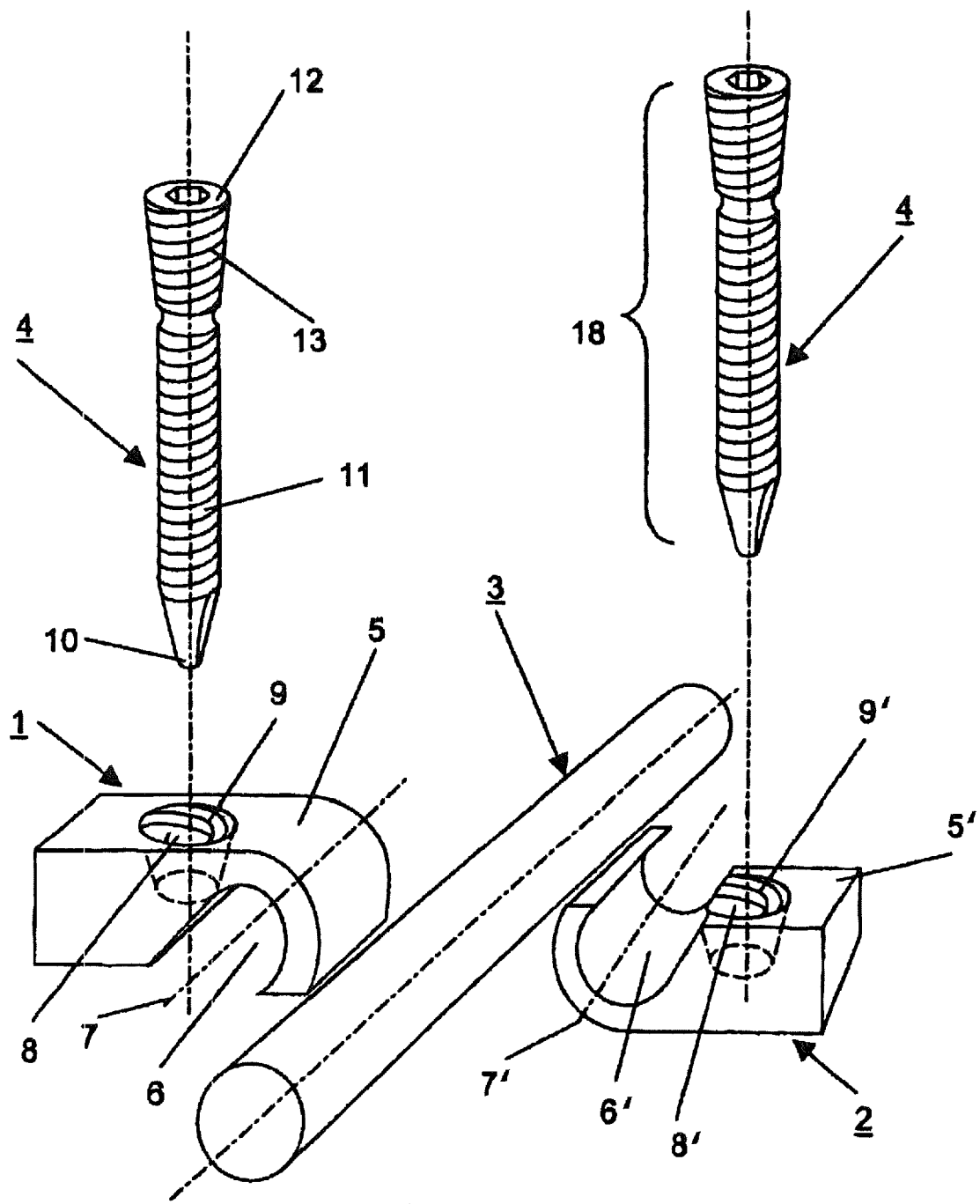
FIG. 1 is an exploded representation of a bone fixation device with a longitudinal carrier, two different types of the inventive device, and two bone screws.

FIG. 1 shows two embodiments of the inventive device. Devices 1, 2 connect a longitudinal carrier 3 to respective bone fixation elements 4. The two embodiments of the device differ primarily in the construction of a channel 6, 6' for accommodating longitudinal carrier 3. For the first embodiment (type A), the channel 6 is open towards the lower surface 16 of the device body 5, which is directed towards the portion of the bone fixation element 4 constructed here as threaded shaft 11. For the second embodiment (type B), channel 6' is open towards the upper surface 17 of body 5', adjoining head 12 of bone fixation element 4. At lower surface 16 (for type A) or at upper surface 17 (for type B) of body 5, 5', respectively, the open surface of channel 6, 6' has a width B transverse to the channel axis 7, 7', which is larger than or equal to the diameter of longitudinal carrier 3. Thus, longitudinal carrier 3 can be introduced transversely into the channel 6, 6' from below (type A) or from above (type B).

For the embodiments shown, bone fixation element 4 is constructed as a bone screw 18 having a tip 10, a threaded shaft 11, and a conical head 12. The threaded shaft 11 can be screwed into a bone, especially a pedicle bone. Conical head 12 has a smaller diameter towards threaded shaft 11. Conical bore 8, which is complementary to head 12, allows threaded shaft 11 to pass through body 5, 5' from upper surface 17 to lower surface 16. The longitudinal axis 19 of bore 8, 8' is skewed with respect to channel axis 7, 7'. For both embodiments, type A and type B, the larger opening 14 of bore 8, 8' discharges into upper surface 17 and the smaller opening 15 discharges into lower surface 16. In particular, for the type A and type B embodiments shown here, longitudinal axis 19 of bore 8, 8' is perpendicular to channel axis 7, 7', a distance X separating longitudinal axis 19 from channel axis 7, 7'. The dimensions of distance X are such that conical bore 8, 8' intersects channel 6, 6'—distance X being larger than the sum of radius R of longitudinal carrier 3 and radius r of threaded shaft 11 of the barren fixation element 4. With that, threaded shaft 11 of bone fixation element 4 can pass through bore 8 8', even when the longitudinal carrier 3 is introduced into channel 6 6', and be screwed into a bone until conical head 12 of bone fixation element 4, which is complementary to bore 8, 8', has been introduced into bore 8, 8' to such an extent that it contacts longitudinal carrier 3. Longitudinal carrier 3 can then be fixed in channel 6, 6' by tightening bone fixation element 4.

For both types A, B of respective devices 1, 2, channel 6, 6' has a concave sidewall 20, which is remote from bore 8, 8' and secures longitudinal carrier 3 placed in channel 6, 6' against displacements parallel to longitudinal axis 19 of bore 8, 8'. When the bone fixation element 4 is tightened in the device, longitudinal carrier 3 placed in channel 6, 6' is (1) pressed by conical head 12 transversely to channel axis 7, 7' against the concave side wall 20 of channel 6, 6' and (2) fixed in channel 6, 6'. Furthermore, bore 8, 8' is provided with an internal thread 9, 9', and the head 12 of bone fixation element 4 is provided with a complementary external thread 13, so that stable locking occurs between bone fixation element 4, body 5, 5' and longitudinal carrier 3 when bone fixation element 4 is tightened.

The invention claimed is:

1. A three piece device consisting of:
   a longitudinal carrier;
   a body including a channel having a longitudinal axis and an opening along the longitudinal axis for receiving the longitudinal carrier, the body having a bore extending completely there through, the channel and the bore partially intersecting each other, the bore constructed conically and having a first opening on one side of the body and a second opening on another side of the body, the first opening larger than the second opening, and the bore having an internal thread; and
   a bone screw including a tip, a threaded shaft for threadably engaging bone, and an externally threaded conical head portion for engaging the internally threaded conical bore such that rotation of the bone screw causes the threaded shaft to engage the bone, the externally threaded head portion to engage the internally threaded bore and the externally threaded head portion to contact the longitudinal carrier positioned with the channel so that the longitudinal carrier is fixed between an inner surface of the channel and the head portion of the bone screw.

2. The device of claim 1 wherein the bore has a conical angle ranging from 5 degrees to 25 degrees.

3. The device of claim 1 wherein the bore has a conical angle ranging from 8 degrees to 15 degrees.

4. The device of claim 1 wherein:
the conical bore tapers inward towards the channel; and
the smaller second opening of the bore is on the same side of the body as the channel.

5. The device of claim 1 wherein
the conical bore expands towards the channel; and
the larger first opening of the bore is on the same side of the body as the channel.

6. The device of claim 1 wherein the external thread has a pitch from about 0.1 to 3.0 millimeters.

7. The device of claim 1 wherein the external thread has a pitch from about 0.25 to 1.50 millimeters.

8. The device of claim 1 wherein the head of the bone screw tapers conically toward the tip.

9. The device of claim 8 wherein the head has a conical angle ranging from 5 degrees to 25 degrees.

10. The device of claim 1 wherein the longitudinal axis of the channel and the bore are perpendicular to each other.

* * * * *